United States Patent [19]

Witzel et al.

[11] 4,409,202

[45] * Oct. 11, 1983

[54] BREATH FRESHENER COMPOSITION AND METHOD

[75] Inventors: Frank Witzel, Spring Valley; Mario A. DiNolfo, Ossining, both of N.Y.; Burton Rodney, Lawrenceville, N.J.; Donald A. M. Mackay, Pleasantville, N.Y.

[73] Assignee: Nabisco Brands, Inc., Parsippany, N.J.

[*] Notice: The portion of the term of this patent subsequent to Dec. 1, 1998 has been disclaimed.

[21] Appl. No.: 283,772

[22] Filed: Jul. 16, 1981

Related U.S. Application Data

[62] Division of Ser. No. 137,944, Apr. 7, 1980, Pat. No. 4,303,648.

[51] Int. Cl.$^3$ ............... A61K 33/06; A61K 33/08; A61K 33/10
[52] U.S. Cl. ........................ 424/49; 424/38; 424/48; 424/154; 424/158; 424/365
[58] Field of Search ............ 424/49, 48, 38, 365, 424/154, 158

[56] References Cited

U.S. PATENT DOCUMENTS

| | | |
|---|---|---|
| 738,461 | 9/1903 | Lewy ................................. 424/156 |
| 780,226 | 1/1905 | Pink .................................. 424/38 |
| 1,630,763 | 5/1927 | Raymer . |
| 2,525,072 | 10/1950 | Kearby . |
| 2,926,121 | 2/1960 | Hobbs et al. . |
| 3,253,988 | 5/1966 | Scott . |
| 3,843,778 | 10/1974 | Diamond et al. . |
| 4,112,066 | 9/1978 | Hussein . |
| 4,163,777 | 8/1979 | Mitra . |
| 4,230,693 | 10/1980 | Izzo et al. ........................ 424/156 |
| 4,271,142 | 6/1981 | Puglia et al. ..................... 424/14 |
| 4,303,648 | 12/1981 | Witzel et al. .................... 424/158 |
| 4,327,076 | 4/1982 | Puglia et al. ..................... 424/38 |
| 4,327,077 | 4/1982 | Puglia et al. ..................... 424/38 |

FOREIGN PATENT DOCUMENTS

| | | | |
|---|---|---|---|
| 54-020159 | 2/1979 | Japan ............................. 424/157 |
| 26894 | of 1908 | United Kingdom ............ 424/156 |
| 294299 | 7/1928 | United Kingdom . |

Primary Examiner—Shep K. Rose
Attorney, Agent, or Firm—Richard Kornutik

[57] ABSTRACT

A breath freshener composition is provided which may be in the form of a comestible, such as a pill, powder, tablet, pressed candy or mint, boiled candy, mouthwash, dental cream, chewing gum and the like, and which includes as its active ingredient a vegetable oil employed in combination with magnesium hydroxide or basic hydrated magnesium carbonate. The above breath freshener composition is especially effective in eliminating onion odor in the mouth and saliva. In addition, a method is provided for inhibiting bad breath wherein any of the above combinations are employed.

11 Claims, No Drawings

BREATH FRESHENER COMPOSITION AND METHOD

This is a division, of application Ser. No. 137,944, filed Apr. 7, 1980, which has issued as U.S. Pat. No. 4,303,648 on Dec. 7, 1982.

The present invention relates to a breath freshener composition which includes as its active ingredient a vegetable oil in combination with magnesium hydroxide or the basic hydrated form of magnesium carbonate, and to a method for inhibiting bad breath employing such compositions.

Magnesium hydroxide employed singly or in combination with calcium hydroxide and/or copper gluconate is known to inhibit putrefaction (the break out of odiferous hydrosulfide groups) of saliva as disclosed in U.S. Pat. No. 4,112,066 to Hussein. However, magnesium hydroxide by itself has not been found to be especially effective in adsorbing or removing onion odor.

U.S. Pat. No. 2,926,121 to Hobbs et al discloses an antacid composition which contains a fully hydrated alumina gel as the primary ingredient and which may contain other antacids, namely, magnesium hydroxide, magnesium trisilicate or calcium carbonate.

British Patent Specification No. 294,299, U.S. Pat. Nos. 2,525,022 to Kearby, 1,630,763 to Raymer and Australian Patent Specification 131,394 disclose chewing gum compositions which include magnesium oxide or hydroxide or calcium carbonate.

U.S. Pat. Nos. 2,894,876 and 3,044,939 to Scanlan et al disclose oral deodorant candy tablets and chewing gum containing copper gluconate preferably in combination with a glyceride fat or oil.

It has now been found that bad breath due to mouth malodor, especially onion odor, is effectively inhibited by comestibles containing a vegetable oil in combination with magnesium hydroxide or the basic hydrated form of magnesium carbonate.

In fact, it has been found that magnesium hydroxide or the basic hydrated form of magnesium carbonate each by itself is not very effective in reducing or eliminating onion odor but a combination of the vegetable oil and either or both magnesium compounds is surprisingly effective for such purpose. Such combinations are substantially more effective in eliminating onion odor than the additive effect of either component of each combination alone thereby indicating that such combinations are synergistic combinations.

It will be appreciated that the term "magnesium hydroxide" will also encompass magnesium oxide. Furthermore, the term "magnesium compounds" as employed herein is intended to encompass magnesium hydroxide (and magnesium oxide) and the basic hydrated form of magnesium carbonate.

The above combinations may be employed in various comestibles, such as pressed candies or mints, boiled candies or drops as well as in dental creams or powders, mouth washes, chewing gums and the like.

It is indeed surprising and unexpected that magnesium hydroxide or the basic hydrated form of magnesium carbonate when used as a substrate for a vegetable oil should adsorb onion odor more effectively than substrates having lower bulk densities (higher surface areas) such as diatomaceous earth and magnesium trisilicate. One would expect that the higher the surface area, the better the substrate. It could only be postulated that the buffering action of magnesium hydroxide or basic hydrated form of magnesium carbonate has a positive effect on the adsorption isotherm.

The vegetable oil will be employed in an amount of within the range of from about 0.07 to about 0.3% and preferably from about 0.1 to about 0.25% by weight of the freshener composition while the magnesium hydroxide substrate will be employed in an amount of within the range of from about 0.4 to about 1.7% and preferably from about 0.5 to about 1.5% by weight of the freshener composition.

The vegetable oil will be employed in a weight ratio to the magnesium hydroxide or basic hydrated form of magnesium carbonate of within the range of from about 0.1:1 to about 0.35:1, and preferably from about 0.15:1 to about 0.25:1. Thus, the concentration of vegetable oil on either of the magnesium compounds may vary from 1% to its maximum saturation point, that is that point which exceeds the uptake of the vegetable oil by either magnesium compound. A preferred concentration range of vegetable oil is from about 15 to about 35% by weight of the combination of the vegetable oil and magnesium compound.

The surface area of the magnesium compounds substrate must be sufficiently large to ensure that the vegetable oil will be properly dispersed so that a maximum amount of the vegetable oil is available for adsorbing odors. Accordingly, the magnesium compounds to be useful herein should have a specific volume of within the range of from about 1.5 to about 6 cc/gm and preferably from about 1.7 to about 4 cc/gm.

As the vegetable oil, any edible triglyceride which has a titer point below 37° C. is acceptable for use as an odor adsorbent. For example, babassu oil, corn oil, coconut oil, cottonseed oil, celine oil, palm kernel oil, peanut oil, rice bran oil, safflower oil, sesame oil, soybean oil, and sunflower oil may be employed. Those oils having titer values dependent on fatty acid chain length rather than degree of unsaturation are preferred. For example, coconut oil composed primarily of lauric acid having a chain length of 12 carbon atoms is preferred over corn oil composed mostly of linolenic acid, an unsaturated acid having a chain length of 18 carbon atoms.

The combination of the vegetable oil and the magnesium compound substrate will be present in an amount within the range of from about 0.5% to about 2.0%, and preferably from about 1% to about 1.5% by weight of the comestible (regardless of the type). Thus, for example, a unit dosage of candy (pressed or boiled), chewing gum, dental cream or mouth wash may contain from about 7.5 to about 30 mg, and preferably from about 15 to about 23 mg of the combination. While amounts greater than 30 mg are effective, and may be employed, if desired, it has been found that amounts of the combination greater than 30 mg may cause taste or flavor problems in a comestible.

In use, the comestible containing the vegetable oil and the various magnesium compound combinations set out above are particularly useful in inhibiting or preventing the onset of bad breath due to onion odor. Thus, for example, the comestible of the invention may be administered after a meal at any time during the day, or even in the morning after a night's sleep.

In preparing the comestibles of the invention, the vegetable oil is simply mixed with the substrate and the combination then mixed with the other ingredients to form the comestible in accordance with accepted manufacturing practice.

The effectiveness of the various combinations of the invention in inhibiting formation of malodorous breath due to onions will be shown by the following Examples which represent preferred embodiments of the present invention.

EXAMPLE 1

Magnesium hydroxide having a specific volume of about 1.7 ml/gm, and a bulk density of 0.6 gm/ml, is admixed with a coconut oil commercially known as Durex 500. The weight ratio of adsorbent (magnesium hydroxide) to oil is 72:28. 15 mg of the magnesium hydroxide adsorbent containing oil is placed in a vial with 3 ml of stimulated saliva, 5 drops of a filtered onion concentrate (42 grams of fresh onion mascerated in 100 cc of $H_2O$) is added and a flavor wick dipped in a saturated solution of silver nitrite is suspended in the headspace.

For purpose of comparison, the magnesium hydroxide substrate is replaced with the following:

Control A—no substrate
Control B—Celite 219, diatomaceous earth having a specific volume of about 5.9 ml/gm, a bulk density of 0.17 gm/ml
Control C—Syloid 63, diatomaceous earth having a specific volume of about 2.3 ml/gm, a bulk density of 0.44 gm/ml
Control D—magnesium trisilicate having a specific volume of about 3.1 ml/gm, a bulk density of 0.32 gm/ml.

In still yet further controls, the substrates used in Controls B, C and D, and Example 1 are employed alone without coconut oil. These further Controls are identified as Control E (Celite 219 alone), Control F (Syloid 63 alone), Control G (magnesium trisilicate alone) and Control H (magnesium hydroxide alone).

After incubation at 37° C. for various times each composition is checked organoleptically for odor and formation of silver sulfide (gray-black) in the wicks. The silver sulfide will form if the headspace includes sulfide odors from onion and stale saliva. The results obtained are set out in Table I below. Controls E, F, G and H are checked only organoleptically after 18 hours.

TABLE I

| Run No. | | Results | 30 Minutes | 2 hrs | 18 hrs |
|---|---|---|---|---|---|
| Control A | Control (no substrate-just oil) | gray-black | +++ | +++ | +++ |
| Control B | Celite 219 (diatomaceous earth) | gray-black | ++ | ++ | ++ |
| Control C | Syloid 63 (diatomaceous earth) | gray-black | +++ | ++ | ++ |
| Control D | Magnesium trisilicate | gray-black | +++ | +++ | +++ |
| Example 1 | Magnesium hydroxide | light tan | + | 0 | 0 |
| Control E | Celite 219 (no coconut oil) | | | | +++ |
| Control F | Syloid 63 (no coconut oil) | | | | +++ |
| Control G | Magnesium trisilicate (no coconut oil) | | | | +++ |
| Control H | Magnesium hydroxide (no coconut oil) | | | | +++ |

0 = no odor
+ = slight odor
++ = fair amount odor
+++ = high odor

A repeat of the above experiment is made using distilled water in place of saliva. Headspace odor would therefore contain only sulfide odors from onion. Evaluations are conducted after 18 hours. The results obtained are shown in Table II below.

TABLE II

| | RESULTS | | |
|---|---|---|---|
| Run No. | | Wick Test | 18 hrs |
| Control A | | gray-black | ++ |
| Control B | Celite 219. | gray-black | ++ |
| Control C | Syloid 63 | gray-black | +++ |
| Control D | Magnesium Trisilicate | gray-black | +++ |
| Example 1 | Magnesium hydroxide | light tan | + |

The above results clearly and surprisingly show that the Example 1 combination of the invention, namely, the coconut oil and magnesium hydroxide combination is far and away superior to combinations of coconut oil and diatomaceous earth (Controls B and C), or magnesium trisilicate (Control D), coconut oil alone (Control A), as well as each of the above substrates or adsorbents employed alone without the oil (Controls E to H) in reducing and eliminating onion odor. Accordingly, it is clear that the combination of the invention is indeed a synergistic combination in that the combination is far superior in performance to the additive performance of that of each of the coconut oil and magnesium hydroxide by itself. In fact, the above results are indeed totally unexpected in that one skilled in the art would expect that the higher specific volume material (indicative of a high surface area) such as Celite 219, Syloid 63 or magnesium trisilicate should absorb odor more effectively than magnesium hydroxide which has the lowest specific volume (lowest surface area) of all the substrate materials tested. The fact that the results are opposite to that which would be normally expected is indeed surprising and unexpected.

The following examples further illustrate the present invention without, however, limiting the same thereto. Each of the following compositions are effective in inhibiting onset of bad breath.

EXAMPLE 2

A pressed mint is prepared from the following formulation:

| | Parts by Weight |
|---|---|
| Mint granulation | 98.1 |
| Coconut oil | 0.38 |
| $Mg(OH)_2$ | 1.12 |
| Flavoring oil | 0.4 |

EXAMPLE 3

A boiled drop is prepared from the following formulation:

|  | Parts by Weight |
|---|---|
| Sugar | 74.0 |
| Corn Syrup 43° Be | 24.0 |
| Flavor | 0.5 |
| Corn oil | 0.38 |
| $Mg(OH)_2$ | 1.12 |

EXAMPLE 4

A mouth wash is prepared from the following formulation:

| | |
|---|---|
| Cottonseed oil | 2.50 gm |
| $4MgCO_3.Mg(OH)_2.5H_2O$ | 7.50 gm |
| Sodium chloride | 8.00 gm |
| Sodium bicarbonate | 2.50 gm |
| Glycerin | 420.00 ml |
| Alcohol | 300.00 ml |
| Menthol | 0.24 gm |
| Thymol | 0.24 gm |
| Methyl salicylate | 0.70 ml |
| Cinnamon oil | 0.50 ml |
| Eucalyptus oil | 1.30 ml |
| Cudbear tincture | 16.00 ml |
| Krameria tincture | 8.00 ml |
| Purified talc | 20.00 gm |
| Purified water sufficient to make | 1,000.00 ml |

EXAMPLE 5

A dental cream is prepared having the following composition:

|  | Parts by Weight |
|---|---|
| Precipitated calcium carbonate | 44.0 |
| Sesame oil | 0.2 |
| $Mg(OH)_2$ | 0.8 |
| Sodium lauryl sulfate | 1.5 |
| Glycerin | 15.0 |
| Sorbitol (70% solution) | 15.0 |
| Na saccharin | 0.1 |
| Methyl p-hydroxy benzoate | 0.1 |
| Na alginate 21 | 1.5 |
| Flavor | 1.1 |
| Purified water | 20.7 |

EXAMPLE 6

A chewing gum is prepared from the following formulation

|  | Parts by Weight |
|---|---|
| Gum base | 20.00 |
| Sorbitol syrup | 12.00 |
| Sorbitol solid | 60.00 |
| Coconut oil | 0.25 |
| $Mg(OH)_2$ | 0.75 |
| Lecithin (Softener) | 0.50 |
| Na Saccharin | 0.10 |
| Peppermint flavor oil | 0.50 |

EXAMPLE 7

A pressed mint is prepared from the following formulation:

|  | Parts by Weight |
|---|---|
| Mint granulation | 97.6 |
| Soybean oil | 0.3 |
| $4MgCO_3.Mg(OH)_2.5H_2O$ | 0.7 |
| Calcium stearate | 1.0 |
| Flavoring oil | 0.4 |

EXAMPLE 8

A boiled drop is prepared from the following formulation:

|  | Parts by Weight |
|---|---|
| Sugar | 73.5 |
| Corn Syrup 43° Be | 25.0 |
| Peanut oil | 0.2 |
| $Mg(OH)_2$ | 0.8 |
| Flavor | 0.5 |

EXAMPLE 9

A mouth wash is prepared from the following formulation:

| | |
|---|---|
| Magnesium hydroxide | 7.00 gm |
| Babassu oil | 3.00 gm |
| Sodium chloride | 8.00 gm |
| Sodium bicarbonate | 2.50 gm |
| Glycerin | 420.00 ml |
| Alcohol | 300.00 ml |
| Menthol | 0.24 gm |
| Thymol | 0.24 gm |
| Methyl salicylate | 0.70 ml |
| Cinnamon oil | 0.50 ml |
| Eucalyptus oil | 1.30 ml |
| Cudbear tincture | 16.00 ml |
| Krameria tincture | 8.00 ml |
| Purified talc | 20.00 gm |
| Purified water sufficient to make | 1,000.00 ml |

EXAMPLE 10

A dental cream is prepared having the following composition:

|  | Parts by Weight |
|---|---|
| Precipitated calcium carbonate | 44.0 |
| Celine oil | 0.28 |
| $Mg(OH)_2$ | 0.72 |
| Sodium lauryl sulfate | 1.5 |
| Glycerin | 15.0 |
| Sorbitol (70% solution) | 15.0 |
| Ca Saccharin (soluble) | 0.1 |
| Methyl p-hydroxy benzoate | 0.1 |
| Na alginate 21 | 1.5 |
| Flavor | 1.1 |
| Purified water | 20.7 |

EXAMPLE 11

A chewing gum is prepared from the following formulation:

|  | Parts by Weight |
|---|---|
| Gum Base | 20 |
| Soybean oil | 0.3 |
| $Mg(OH)_2$ | 0.7 |
| Sucrose | 50 |

-continued

| | Parts by Weight |
|---|---|
| Sorbitol | 10 |
| Corn Syrup | 19 |

Each of the comestible formulations of Examples 2 to 11 is prepared by first forming a combination of the vegetable oil and magnesium compound, and mixing such combination with the other comestible ingredients to form the final product following accepted comestible making techniques. These comestibles are found to be effective in reducing or eliminating bad breath due to onion odor.

What is claimed is:

1. A breath freshener candy composition consisting essentially of a combination of vegetable oil and a substrate comprising magnesium hydroxide or the basic hydrated form of magnesium carbonate, dispersed in a non-toxic candy carrier, said vegetable oil being present in the weight ratio to the substrate of within the range of from about 0.1:1 to about 0.35:1.

2. The candy composition as defined in claim 1 wherein said substrate is present in an amount within the range of from about 0.4 to about 1.7% by weight.

3. The candy composition as defined in claim 1 wherein said substrate is magnesium hydroxide.

4. The candy composition as defined in claim 1 wherein said vegetable oil is present in an amount of within the range of from about 0.07 to about 0.3% by weight.

5. The candy composition as defined in claim 1 wherein said vegetable oil is present in a weight ratio to the substrate of within the range of from about 0.15:1 to about 0.25:1.

6. The candy composition as defined in claim 1 wherein said vegetable oil is babassu oil, corn oil, coconut oil, cottonseed oil, celine oil, palm kernel oil, peanut oil, rice bran oil, safflower oil, sesame oil, soybean oil, or sunflower oil.

7. The candy composition as defined in claim 1 wherein said vegetable oil is coconut oil and said substrate is magnesium hydroxide.

8. The candy composition as defined in claim 7 wherein the coconut oil is present in an amount within the range of from about 0.07 to about 0.3% by weight and the magnesium hydroxide is present in an amount within the range of from about 0.4 to about 1.7% by weight.

9. A method for inhibiting bad breath which comprises the introduction of a composition as defined in claim 1 into the oral cavity.

10. A method for inhibiting bad breath which comprises the introduction of a composition as defined in claim 3 into the oral cavity.

11. A method for inhibiting bad breath which comprises the introduction of a composition as defined in claim 7 into the oral cavity.

* * * * *